US00PP28158P2

(12) United States Plant Patent
Stemkens

(10) Patent No.: US PP28,158 P2
(45) Date of Patent: Jul. 4, 2017

(54) ***PHLOX* PLANT NAMED 'PHOZ0001'**

(50) Latin Name: *Phlox subulata*
Varietal Denomination: PHOZ0001

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/999,433

(22) Filed: May 3, 2016

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — Dale Skalla

(57) ABSTRACT

A new *Phlox* plant named 'PHOZ0001' particularly distinguished by large flowers, plant vigor, and upright habit.

1 Drawing Sheet

Latin name of the genus and species of the plant claimed: *Phlox subulata.*

Varietal denomination: 'PHOZ0001'.

BACKGROUND OF THE NEW PLANT

The present invention comprises a new and distinct variety botanically known as *Phlox subulata*, and hereinafter referred to by the variety name 'PHOZ0001'.

The new variety originated from a controlled hybridization in April of 2010 in Enkhuizen, The Netherlands between the female parent, proprietary *Phlox* plant 'J7807-1' (unpatented), and the male parent, proprietary *Phlox* plant 'J7803-1' (unpatented).

'PHOZ0001' was first propagated by cuttings in Enkhuizen, The Netherlands in 2011 and has been subsequently asexually propagated. 'PHOZ0001' has been found to retain its distinctive characteristics through successive asexual propagations via vegetative cuttings for more than 5 generations.

BRIEF SUMMARY OF THE INVENTION

The following are the most outstanding and distinguishing characteristics of this new variety when grown under normal horticultural practices in Enkhuizen, The Netherlands: 1. Large flowers, 2. Plant vigor, and 3. Upright habit.

A Plant Breeder's Right for 'PHOZ0001' has not been filed yet. 'PHOZ0001' has not been sold or made publicly available more than one year prior to filing of this application.

BRIEF DESCRIPTION OF THE PHOTOGRAPHS

This new *Phlox* plant is illustrated by the accompanying photograph which shows the flower blooms and foliage of the plant. The colors shown are as true as can be reasonably obtained by conventional photographic procedures. Differences in the coloration of the blooms in the photograph are due to age differences between the flowers. The photograph was taken in Enkhuizen, The Netherlands in March of 2016.

BRIEF DESCRIPTION OF THE NEW VARIETY

The following detailed description sets forth the distinctive characteristics of 'PHOZ0001'. The data which defines these characteristics were collected from asexual reproductions carried out in Enkhuizen, The Netherlands. The plant history was taken on approximately 6 month old plants. Color readings were taken under natural light.

Color references are made to The Royal Horticultural Society Colour Chart (R.H.S.) 2001.

TABLE 1

DIFFERENCES BETWEEN THE NEW VARIETY 'PHOZ0001' AND A MOST SIMILAR VARIETY

| | 'PHOZ0001' | 'McDaniels Cusion' (Unpatented) |
|---|---|---|
| Flower color: | Lighter, RHS 78B | Deep rose, RHS 74D |
| Flower size: | Larger | Smaller |
| Plant habit: | Upright | Prostrate habit |

Plant:

*Plant habit.*—Vigorous, upright and mounded.

*Growth habit.*—Vigorous and freely-branching.

*Form.*—Strong.

*Height (measured from the top of the soil).*—17.0-24.0 cm.

*Diameter or area of spread.*—23.0-30.0 cm.

*Diameter or area of spread (2-year old plant).*—Approximately 60.0 cm.

*Propagation.*—Vegetative cuttings.

*Time to produce a finished flowering plant.*—25 to 30 weeks.

*Lastingness of inflorescence on the plant.*—4 days.

*Outdoor plant performance.*—Good.

*Time to initiate and develop roots.*—3 weeks.

*Time to produce rooted cutting or liner (young plant).*—5 weeks.

*Root description*.—Many tiny roots.
*Branches*.—Habit — Semi-upright.
*Number of branches per plant*.—At least 25, quickly dividing into new branches.
*Length of lateral branches*.—23.0-32.0 cm.
*Diameter of spread of lateral branches*.—20.0 cm.

Stems:
*Shape in cross-section*.—Oval.
*Color*.—RHS 199C.
*Diameter*.—1.8 mm.
*Pubescence*.—Very short hairs.

Leaves:
*Arrangement*.—Opposite.
*Color*.—Immature leaf (both upper and lower surfaces): RHS 137B. Mature leaf (both upper and lower surfaces): RHS 137A.
*Apex*.—Acute.
*Base*.—Truncated.
*Margin*.—Smooth.
*Length*.—22.0 mm.
*Width*.—3.5 mm.
*Shape*.—Acicular.
*Texture*.—Smooth.
*Venation*.—One single vein in the middle of the leaf.
*Petiole*.—Absent.

Peduncle:
*Color*.—RHS 199C.
*Length*.—22.0 mm.
*Diameter*.—0.8-0.9 mm.

Inflorescence:
*Infloresecnce type*.—Cyme.
*Blooming habit*.—Abundant flowers.
*Height*.—45.0 mm.
*Width*.—60.0 mm.
*Natural flowering season*.—Spring (April to May).
*Flower number per inflorescence*.—3 to 8.
*Fragrance*.—Musk fragrance.

Flowers:

Flower bud:
*Length*.—18.0 mm.
*Width*.—3 mm.
*Color*.—RHS 137B.

Pedicel:
*Color*.—RHS 137B.
*Length*.—16.0 mm.
*Diameter*.—0.9 mm.

Sepals:
*Number*.—5.
*Shape*.—Fused.
*Length*.—12.0 mm.
*Width*.—3.0 mm.
*Color* (*both upper and lower surfaces*).—RHS 137C.

Corolla:
*Length*.—17.0 mm.
*Width*.—5.0 mm.

Petals:
*Length*.—20.0 mm.
*Width*.—11.0 mm.
*Number*.—5.
*Shape*.—Obcordate, fused at base.
*Color*.—Upper surface (base color): RHS N78D. Upper surface (at center): RHS 79D (a very small eye). Outside of corolla tube: RHS N78D.

Reproductive organs:

Stamens:
*Quantity* (*per flower*).—5.
*Anther color*.—RHS 12C.
*Pollen color*.—RHS 12D.

Pistil:
*Quantity*.—1.
*Color*.—RHS 137D.
*Size*.—2.0 mm.

Style:
*Length*.—9.0 mm.
*Shape*.—Three lobes.
*Disease and insect resistance*.—Not observed to date.
*Pest resistance*.—Not observed to date.

What is claimed is:

1. A new and distinct variety of *Phlox* plant named 'PHOZ0001' substantially as illustrated and described herein.

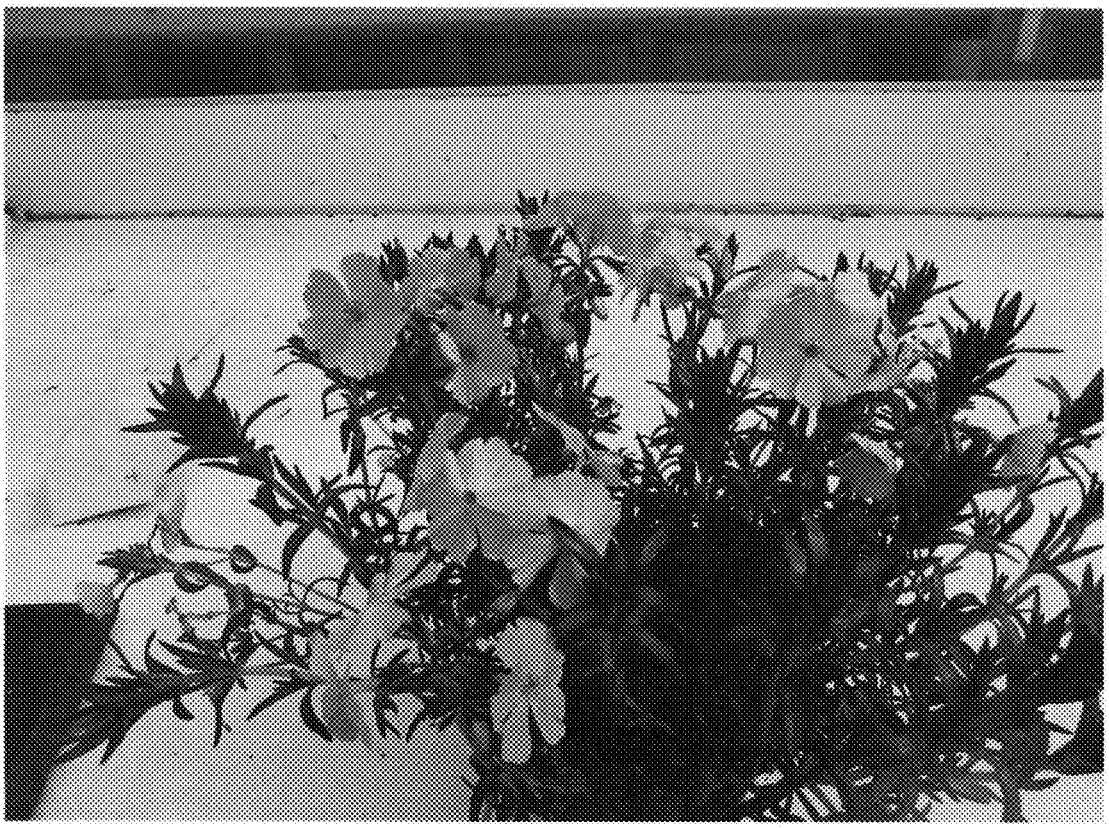

* * * * *